United States Patent [19]

Geng

[11] Patent Number: 5,637,080
[45] Date of Patent: Jun. 10, 1997

[54] WOUND DRESSING

[76] Inventor: Lisa F. Geng, 79 Kerrigan St., Long Beach, N.Y. 11561

[21] Appl. No.: 567,341

[22] Filed: Nov. 8, 1995

Related U.S. Application Data

[63] Continuation of Ser. No. 289,845, Aug. 12, 1994, abandoned, which is a continuation of Ser. No. 56,733, May 4, 1993, abandoned.

[51] Int. Cl.$^6$ .................................................. A61F 13/00
[52] U.S. Cl. ............................... 602/58; 602/42; 602/47; 604/307
[58] Field of Search ........................ 602/41, 42, 57, 602/58, 59, 44–47; 128/857, 887, 888; 604/304, 307

[56] References Cited

U.S. PATENT DOCUMENTS

| | | |
|---|---|---|
| 3,262,277 | 7/1966 | Nesbitt . |
| 3,367,329 | 2/1968 | Dibelius . |
| 3,425,412 | 2/1969 | Pope .................................. 602/42 |
| 3,826,253 | 7/1974 | Larsh et al. .................... 128/854 |
| 4,399,816 | 8/1983 | Spangler ......................... 128/888 |
| 4,513,739 | 4/1985 | Johns . |
| 4,649,909 | 3/1987 | Thompson ........................ 602/42 |
| 4,706,662 | 11/1987 | Thompson ........................ 602/44 |
| 4,711,781 | 12/1987 | Nick et al. . |
| 4,737,400 | 4/1988 | Edison et al. . |
| 4,917,112 | 4/1990 | Kalt . |
| 4,981,133 | 1/1991 | Rollband . |
| 5,009,224 | 4/1991 | Cole . |
| 5,086,763 | 2/1992 | Hathman ......................... 602/42 |
| 5,127,423 | 7/1992 | Draeger .......................... 128/854 |
| 5,149,469 | 9/1992 | Komatsuzaki et al. . |
| 5,167,613 | 12/1992 | Karami et al. ................... 602/57 |
| 5,244,523 | 9/1993 | Tollini . |
| 5,520,629 | 5/1996 | Heinecke et al. . |

*Primary Examiner*—Vincent Millin
*Assistant Examiner*—Chalin Smith
*Attorney, Agent, or Firm*—Darby & Darby

[57] ABSTRACT

An external wound dressing having a cover which is reversibly movable to an open position exposing the wound from a closed position covering the wound thereby enabling selective viewing of the wound without removing the wound dressing from the individual.

33 Claims, 3 Drawing Sheets

WOUND DRESSING

This is a continuation application of U.S. Ser. No. 08/289,845 filed on Aug. 12, 1994 now abandoned which is a continuation application of U.S. Ser. No. 08/056,733 filed on May 4, 1993 now abandoned.

FIELD OF THE INVENTION

The present invention is generally directed to a wound dressing and particularly to a wound dressing which enables the wound to be viewed by a person such as patient, doctor, mother, child, etc. without removing the wound dressing. A cover means, particularly in the form of a flap, is provided which is movable to an open position to allow viewing of the wound from a closed position whereby viewing of the wound is prevented.

BACKGROUND OF THE INVENTION

Wound dressings, including Band-Aid® brand wound dressings, generally include an opaque backing layer having an adhesive applied to one side for adhering to the skin. A protective layer, typically made of a release paper is applied to the adhesive side of the backing layer and is releasable therefrom when the wound dressing is applied to the skin. The area immediately covering the wound often has a gauze pad which may be impregnated with an antibacterial agent or the like.

Wound dressings as described above and as disclosed, for example, in N. R. Dibelius, U.S. Pat. No. 3,367,329, must be removed in order for the individual and/or the physician to view the wound. Once the wound dressing is removed it may become contaminated or difficult to put back on the wound. Therefore, removal of the wound dressing often necessitates replacing the old wound dressing with a new one, which can be stressful to the individual.

Excessive use of wound dressings is also apparent when young children obtain superficial wounds such as minor cuts, abrasions and the like. Children are naturally curious and they often prematurely remove a wound dressing to view their wound and to show it to their friends. Each time a wound dressing is removed, it is often difficult to reapply the same wound dressing because the adhesive layer loses its tackiness and the like. Accordingly, the number of wound dressings used during the healing of minor cuts and abrasions, particularly with children, is often greater than what might otherwise be expected.

A wound dressing was developed which enables the wound to be viewed without removing the wound dressing. In particular, O. L. Johns, U.S. Pat. No. 4,513,739, discloses an external wound dressing which may have a backing material made entirely out of a transparent polyurethane film. When the wound dressing is applied to the skin, the wound is always visible. While such a wound dressing enables the individual to view the wound without removing the dressing, permanent visibility has its disadvantages.

In particular, many individuals do not want to see their wound. In some cases, the wound is unpleasant to look at. Indeed, some individuals find the viewing of particularly onerous wounds very stressful and unpleasant and, therefore, would prefer wound dressings which completely hide the wound from view. As a result, the individual and/or physician must decide between opaque wound dressings which do not allow the wound to be viewed in the absence of removing the wound dressing, and transparent wound dressings in which the wound is permanently open to view. Quite obviously, each such wound dressing has its disadvantages.

It would be a significant advance in the wound dressing industry to provide a wound dressing in which (a) the wound could be viewed by the individual and/or physician without removing the wound dressing and (b) the wound could be covered when the viewing of the wound is not desired.

SUMMARY OF THE INVENTION

The present invention is generally directed to a wound dressing which permits selective viewing of a wound without having to remove the wound dressing from the skin. When viewing of the wound is completed, the wound may be covered by the individual or physician if desired and then viewed again at a later time without reapplying an entirely new wound dressing.

More particularly, one embodiment of the present invention is directed to an external wound dressing comprising:

(a) a first layer comprising a backing sheet material having a first portion for positioning over the wound and a second portion, said first portion being made of a material which enables the wound to be seen through the first layer;

(b) an adhesive on a first face of at least the second portion of the first layer of backing sheet material;

(c) a second layer comprising a protective sheet material covering the first layer and being in releasable contact with the adhesive, said second layer being removable from the adhesive to enable the wound dressing to be applied to the wound; and (d) cover means covering the first portion of the first layer and being reversibly movable from a closed position covering the wound to an open position so that the wound can be viewed by the user.

In an alternative embodiment, the first portion comprises an opening in the backing sheet material through which the wound may be seen when the cover means is moved to the open position.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
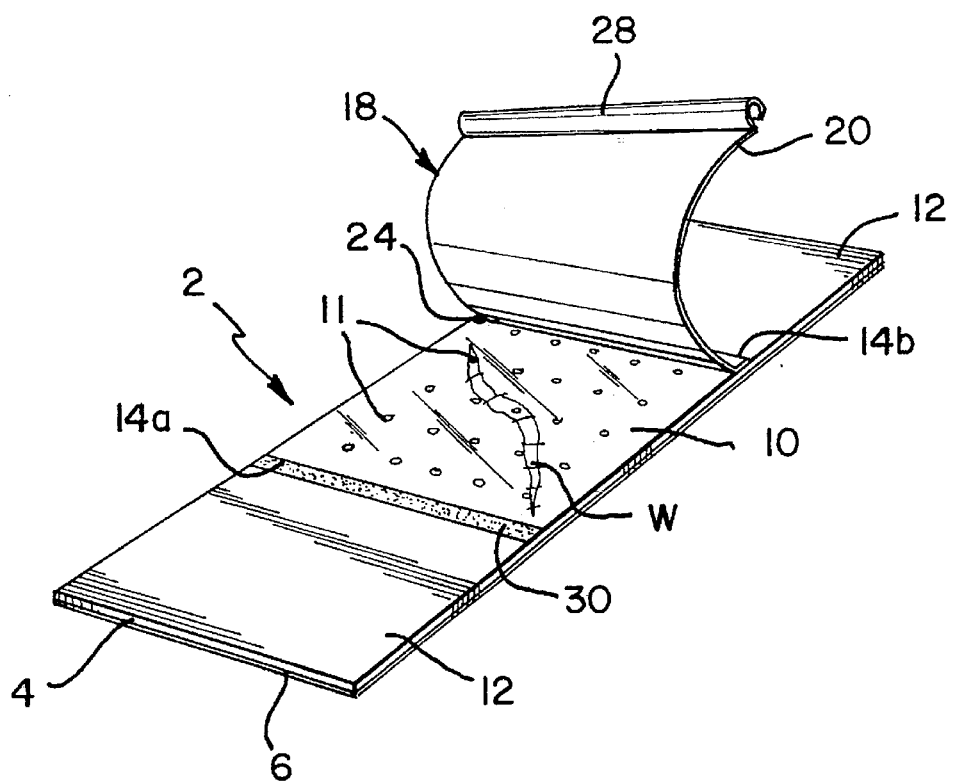
FIG. 1 is a perspective view of one embodiment of a wound dressing in accordance with the present invention with a flap in the open position for viewing the wound.
Figure 2:
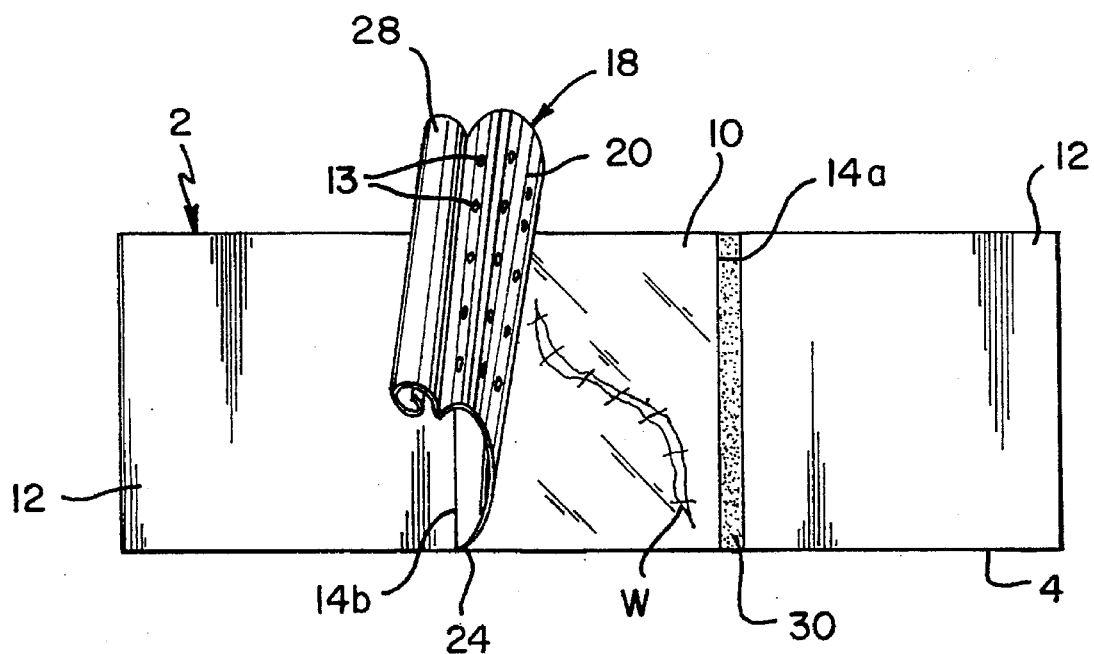
FIG. 2 is a plan view of the embodiment of the invention shown in FIG. 1 rotated 180°.
Figure 3:
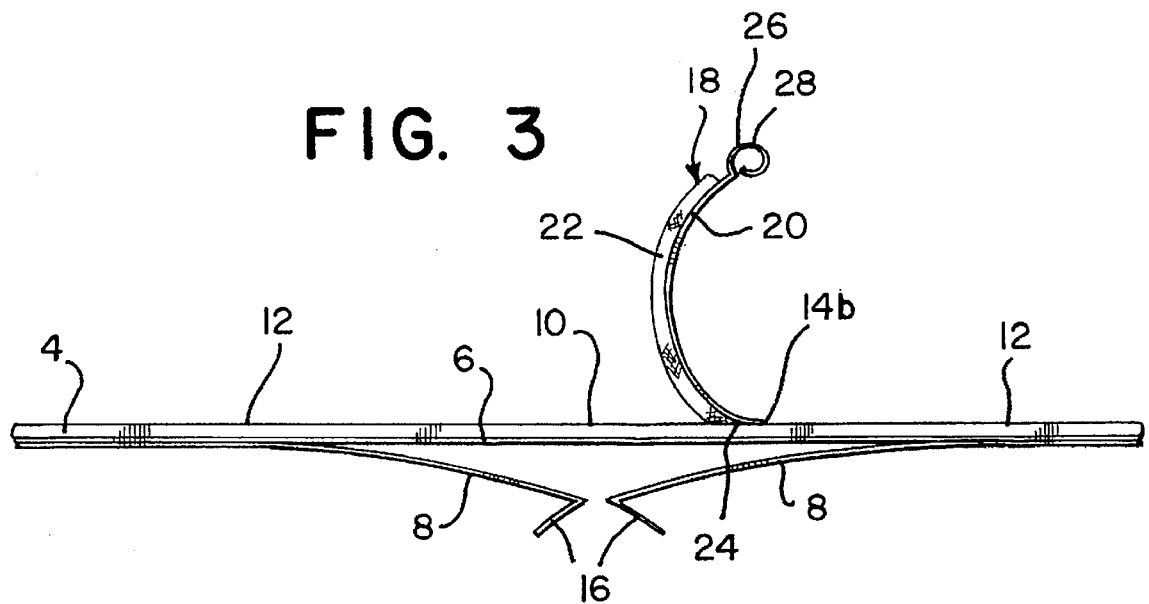
FIG. 3 is a side view of the embodiment shown in FIG. 1.

Referring to FIGS. 1–3, there is shown a first embodiment of the wound dressing of the present invention particularly adapted for covering superficial wounds and abrasions such as those typically covered by Band-Aid® brand wound dressings. The wound dressing 2 includes a layer of backing sheet material 4 having an adhesive 6 on the bottom surface thereof and a release paper 8 (see FIG. 3) releasably attached to the adhesive 6.

The backing sheet material 4 has a first portion 10 which is intended to be positioned directly over the wound identified by the letter "W". In accordance with one aspect of the present invention, the first portion 10 of the backing sheet material 4 enables a person to view the wound without removing the wound dressing 2.

The first portion 10 of the backing sheet material 4 may be transparent or may comprise a cut-out portion or opening as discussed hereinafter in connection with FIG. 6. The transparent first portion 10 as shown in FIGS. 1–3 may be made of such known materials as a transparent polyurethane film of about 0.5 to 2 mils (13 to 51 microns) which may or may not be permeable to gases and/or liquids as identified in Johns, U.S. Pat. No. 4,513,739, and Hodgson, U.S. Pat. No. 3,645,835, incorporated herein by reference. Permeability may be imparted to the polyurethane film by providing a plurality of spaced apart perforations through the film as shown by numeral 11. Alternatively, the first portion 10 may be made of a mesh type material which enables at least partial viewing of the wound.

The backing sheet material 4 has a second portion 12 extending outwardly on both ends 14a, 14b of the first portion 10. The second portion 12 may be made of the same material as the first portion or may be made of more traditional opaque materials which are two-way stretchable, non-toxic, and porous. Examples of such materials are Nylon, Dacron polyethylene, cotton and linen, such as disclosed in N. R. Dibelius, U.S. Pat. No. 3,367,329, incorporated herein by reference.

The backing sheet material 4 is attached to the skin through an adhesive layer 6. The adhesives which may be used may be any conventional adhesive which is non-toxic and readily adheres to the skin. One such example is disclosed in S. M. Cole, U.S. Pat. No. 5,009,224, incorporated herein by reference, which discloses a pressure-sensitive adhesive having a discontinuous gaseous phase.

The adhesive layer 6 is covered with a release paper 8 which will protect the adhesive during storage of the wound dressing and be easily released therefrom when the wound dressing is to be placed over the wound. The release paper 8 may be any sheet material having these properties such as paper, polyethylene and polypropylene. A suitable release material, for example, is a 40 to 75 pound basis weight paper coated on one or both sides with a suitable finish such as clay and with a release agent such as silicone. The thickness of the release layer 8 will normally be about 2 to 6 mils (51 to 152 microns). A pull tab 16 may be attached to the release layer 8 as shown best in FIG. 3. Other types and arrangements of release paper 8 may be found in O. L. John, U.S. Pat. No. 4,513,739.

In accordance with the present invention, the first portion 10 of the backing sheet material 4 is covered with a flap 18 which is movable from an open position as shown in FIGS. 1–3 wherein the first portion 10 of the backing sheet material 4 is exposed, to a closed position (not shown) covering the first portion 10 of the backing sheet material 4.

The flap 18 is comprised of a backing material 20 which may be the same material used for the second portion 12 of the backing sheet material 4. As shown in FIG. 2, the flap 18 may optionally include perforations 13 to impart permeability as described above for the transparent film shown in FIG. 1. The flap 18 may optionally include a layer of gauze 22 (see FIG. 3) which adheres to the backing material 20 by a conventional adhesive. Adhesives exemplified for use with the underside of the backing sheet material 4, previously described, may be used for this purpose.

The flap 18 has a first end 24 either permanently or removably attached to the backing sheet material 4 at the end 14b of the first portion 10. Attachment may be by use of an adhesive, by hot pressing, stitching or other suitable means. The opposed end 26 has a surface 28 which contacts a corresponding surface 30 of the backing material 4 located at the end 14a of the first portion 10 when the flap 18 is moved to the closed position. Either of the surfaces 28 and 30 may be provided with a suitable adhesive or other means of releasable attachment such as a loop and hook fabric sold under the trademark VELCRO.

If the flap 18 is attached permanently to the end 14b of the backing sheet material 4, the flap 18 can be pivoted about the end 14b to expose or cover the wound. Alternatively, if the flap 18 is only temporarily attached at the ends 14a and 14b, the flap 18 may be lifted upwards from the backing sheet material 4 to expose the wound and then again placed into contact with the backing sheet material 4 to cover the wound. In this embodiment of the invention, the same flap 18 may be placed over the wound or an entirely new flap may be placed over the wound.

In operation, the wound dressing 2 of the present invention is placed upon the wound "W" in the same manner as other typical wound dressings. Specifically, the release paper 8 is removed from the adhesive 6 by pulling on the respective pull tabs 16. The wound dressing 2 is then pressed against the skin so that the second portion 12 of the backing material adheres to the individual while the first portion 10 covers the wound.

In order to view the wound without removing the wound dressing, the flap 18 is pulled upwardly so that the respective surfaces 28 and 30 disengage from each other and the wound beneath the flap 18 is exposed if the flap 18 is permanently attached to the end 14b. Alternatively, if the flap 18 is temporarily attached at both ends 14a and 14b, such as by a release type adhesive, the flap 18 may be entirely removed from the backing sheet material 4. When viewing of the wound is no longer desired, the flap 18 is moved downwardly by the user until the surfaces 28 and 30 are reengaged and the flap 18 thereby covers the wound. Alternatively, the flap 18 is again placed over the wound so that the cover is reengaged at both ends 14a and 14b.

Figure 4:
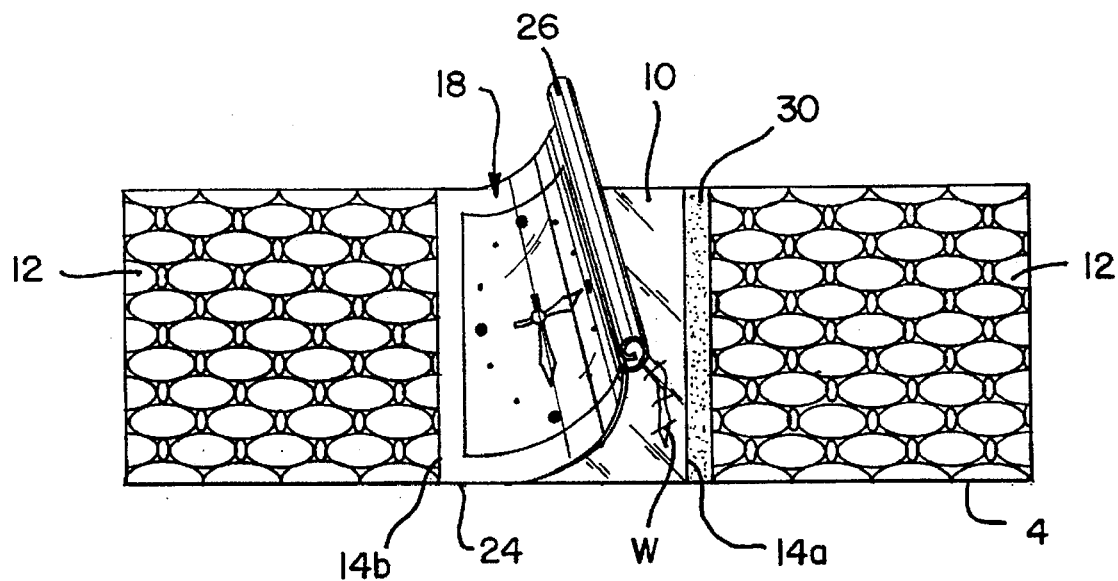
FIG. 4 is another embodiment of the present invention similar to FIG. 1 in which the upper surfaces of the wound dressing are imprinted with indicia.

The wound dressing of the present invention may be decorated with various designs and/or illustrations, particularly for younger children. One such example is shown in FIG. 4. The upper surface of the second portion 12 of the sheet backing material 4 has a design in the form of a watch band while the upper surface of the flap 18 is decorated with a watch face.

Figure 5:
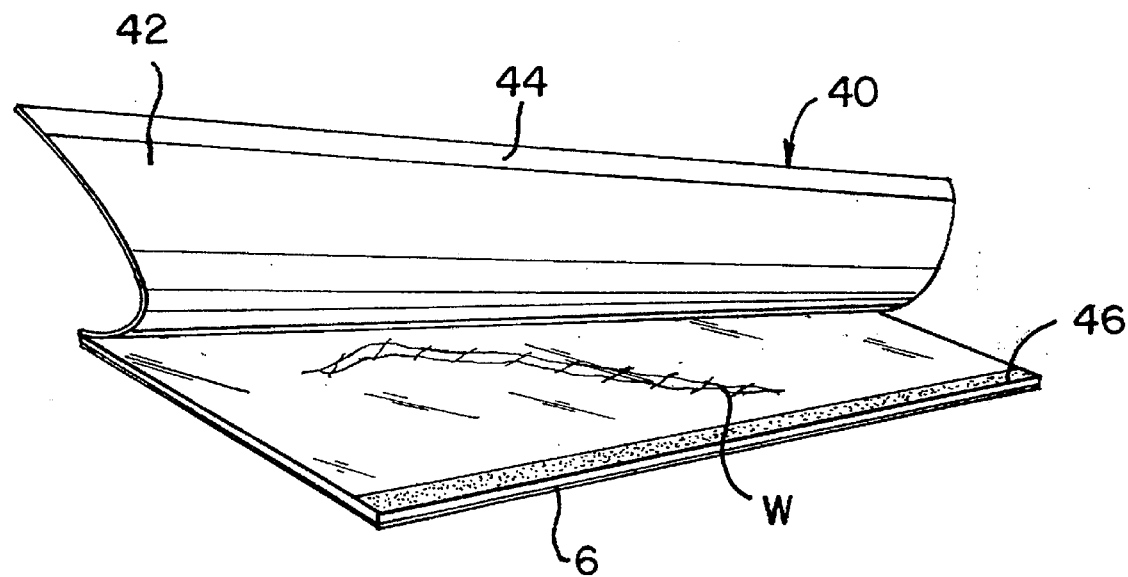
FIG. 5 is a perspective view of another embodiment of the wound dressing of the present invention which is adapted for covering large surgical wounds.

The wound dressing of the present invention may be made in a variety of shapes and sizes within the spirit and scope of the invention. For example, referring to FIG. 5, there is shown a large surgical bandage used for covering major surgical wounds such as encountered with chest surgery. The wound dressing 40 has a flap 42 which is attached along one end of the length of the wound dressing to facilitate moving the flap from the open to the closed position. The end 44 of the flap 42 is adapted to reversibly engage a corresponding end 46 to cover the wound when the flap 42 is pushed downwardly over the wound.

In another embodiment of the invention, the first portion of the backing sheet material comprises an opening in the backing sheet material 4. The flap is, like the embodiments of the invention previously described, reversibly movable to an open from a closed position to expose and cover the wound, respectively.

Figure 6:
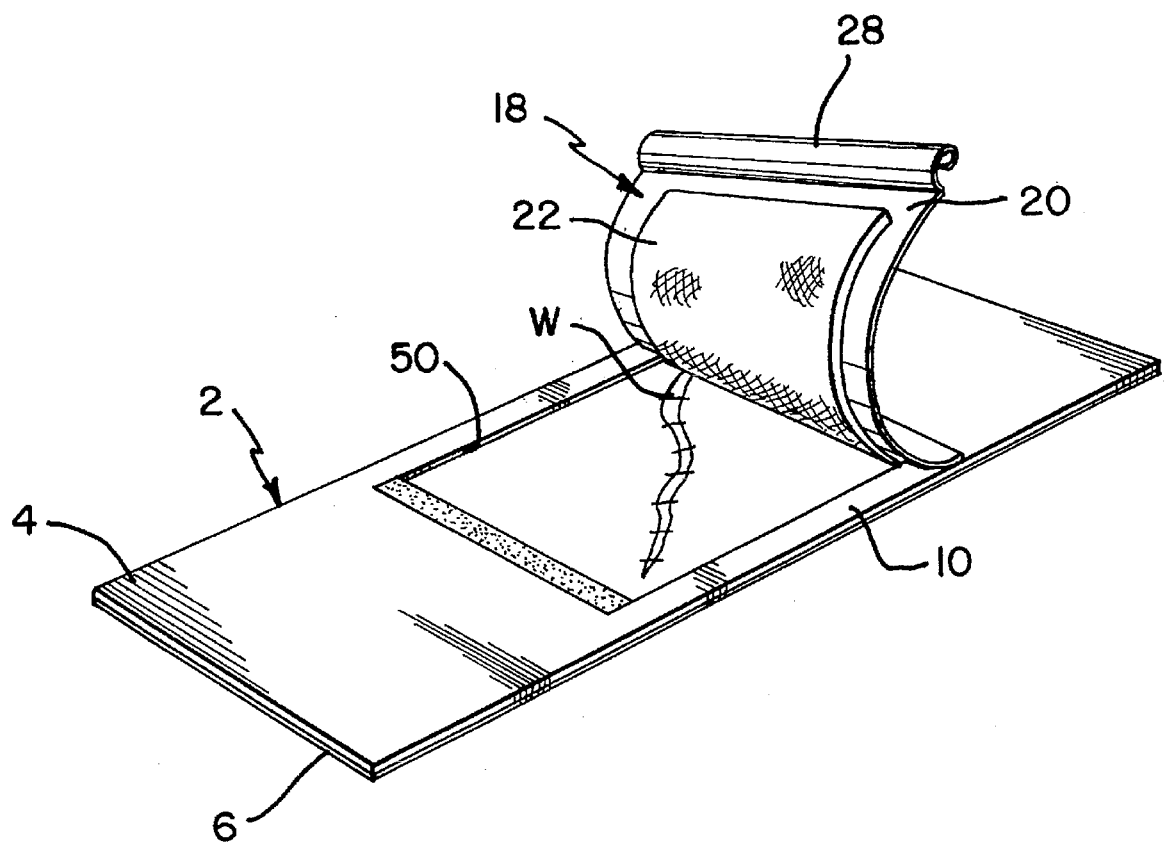
FIG. 6 is a perspective view of still another embodiment of the invention in which the backing layer which adheres to the skin has a cut-out portion exposing the wound.

Referring specifically to FIG. 6, the wound dressing 2 has a first portion 10 comprising an opening 50 directly over the wound W. The wound dressing includes a flap 18 like the previously described embodiments which is adapted to cover the wound. In this embodiment, the flap 18 provides the sole protection for the wound.

Other modifications of the invention would be apparent to those of ordinary skill in the art. For example, the wound dressing may be provided with a customary antibacterial agent by impregnating the same in the first portion 10 of the backing sheet material 4 and/or the gauze 22 on the underside of the flap 18.

I claim:

1. An external wound dressing comprising:
    a first layer comprising a backing sheet material having a first portion for positioning over a wound and being made of a material which enables the wound to be seen through said first layer, said first layer further comprising a first face facing the wound and a second face facing away from the wound, said first portion having a first end and a second end;
    an adhesive on at least a portion of said first face of said first layer of backing sheet material, said adhesive being selected for ready adherence to the skin of a patient;
    a flap having a first end and a second end, said first end of said flap being directly coupled to said first layer adjacent said first end of said first portion of said first layer;
    a releasable attachment element on said second end of said flap, said attachment element permitting attachment of said second end of said flap directly to said second face of said first layer adjacent said second end of said first portion of said first layer to thereby cover said first portion of said first layer with said flap, said attachment element further permitting repeated releasing and reattaching of said second end of said flap directly to said second face of said first layer such that said flap is movable between a closed position covering the wound to an open position permitting viewing of the wound by the user;
    wherein:
    said flap has a first face facing said second face of said first layer, said first face of said flap being free of attachment elements directly adjacent said first layer and between said first end and said second end of said flap to facilitate repeated releasing and reattaching of said second end of said flap to uncover and cover the wound below said first portion of said first layer without having said first face of said flap adhere to said first portion of said first layer; and
    said backing sheet material and said flap are made of a non-rigid, flexible material that readily conforms to the area over which said wound dressing is applied and is not so rigid as to maintain a predetermined shape before application over a wound.

2. An external wound dressing as in claim 1, wherein said first portion of said first layer is perforated.

3. An external wound dressing as in claim 1, wherein said first portion of said first layer is formed from a mesh material.

4. An external wound dressing as in claim 1, wherein said adhesive comprises a pressure sensitive, non-toxic adhesive.

5. An external wound dressing as in claim 1, wherein said first face of said flap is covered with an adhesive, said flap further comprising a layer of gauze attached to said adhesive such that said adhesive is not directly adjacent said first layer.

6. An external wound dressing as in claim 1, wherein said attachment element comprises an adhesive.

7. An external wound dressing as in claim 1, further comprising a release paper covering said adhesive on said first layer and removable from said adhesive to enable said wound dressing to be applied to the wound.

8. An external wound dressing as in claim 1, wherein said attachment element comprises hook and loop material.

9. An external wound dressing as in claim 1, wherein said first end of said flap is permanently coupled to said first layer.

10. An external wound dressing as in claim 8, wherein said first end of said flap is coupled to said first layer by hot pressing.

11. An external wound dressing as in claim 9, wherein said first end of said flap is coupled to said first layer by stitching.

12. An external wound dressing as in claim 1, wherein said first end of said flap is removably coupled to said first layer with a releasable attachment element.

13. An external wound dressing as in claim 12, wherein said releasable attachment element on said first end of said flap is formed from the same material as said releasable attachment element on said second end of said flap.

14. An external wound dressing as in claim 1, wherein said first portion of said first layer comprises a substantially transparent material.

15. An external wound dressing as in claim 14, wherein said first portion of said first layer comprises a polyurethane film.

16. An external wound dressing as in claim 15, wherein said film is gas permeable.

17. An external wound dressing as in claim 1, wherein said first layer further comprises a second portion extending from at least one of said first and second ends of said first portion, said second portion being formed from a non-rigid, flexible material that readily conforms to the area over which said wound dressing is applied and is not so rigid as to maintain a predetermined shape before application over a wound.

18. An external wound dressing as in claim 17, wherein said second portion extends from both of said first and second ends of said first portion.

19. An external wound dressing as in claim 17, wherein said second portion is opaque.

20. An external wound dressing as in claim 17, wherein said second portion is formed from a non-toxic, porous material.

21. An external wound dressing as in claim 17, wherein second portion is made from the same material as said first portion.

22. An external wound dressing as in claim 17, wherein said adhesive on at least a portion of said first face of said first layer extends over said second portion of said first layer.

23. An external wound dressing as in claim 17, wherein:
    said flap has a second face facing away from the wound; and
    said second faces of said second portion and said flap are decorated with a design.

24. An external wound dressing as in claim 17, wherein said second portion is formed from a two-way stretchable material.

25. An external wound dressing as in claim 24, wherein said second portion is formed from a non-toxic, porous material.

26. An external wound dressing as in claim 17, wherein said second portion is formed from a non-rigid, flexible fabric.

27. An external wound dressing as in claim 26, wherein said fabric is selected from the group consisting of Nylon, Dacron, polyethylene, cotton and linen.

28. An external wound dressing comprising:

a first layer comprising a backing sheet material which enables the wound to be seen, said first layer having a first face facing the wound, a second face facing away from the wound, a first end, and a second end;

an adhesive on at least a portion of said first face of said first layer, said adhesive being selected for ready adherence to the skin of a patient;

a flap having a first end and a second end, said first end of said flap being directly coupled to said first end of said first layer;

a releasable attachment element on said second end of said flap, said attachment element permitting attachment of said second end of said flap directly to said second end of said first layer to thereby cover said first layer with said flap, said attachment element further permitting repeated releasing and reattaching of said second end of said flap directly to said second face of said first layer such that said flap is movable between a closed position covering the wound to an open position permitting viewing of the wound by the user; wherein:

said flap has a first face facing said second face of said first layer, said first face of said flap being free of attachment elements directly adjacent said first layer and between said first end and said second end of said flap to facilitate repeated releasing and reattaching of said second end of said flap to uncover and cover the wound below said first layer without having said first face of said flap adhere to said first layer; and said backing sheet material and said flap are made of a non-rigid, flexible material that readily conforms to the area over which said wound dressing is applied and is not so rigid as to maintain a predetermined shape before application over a wound.

29. An external wound dressing as in claim 28, wherein said backing sheet material comprises a substantially transparent material.

30. An external wound dressing as in claim 29, wherein said backing sheet material comprises a polyurethane film.

31. An external wound dressing as in claim 28, wherein said backing sheet material is gas permeable.

32. An external wound dressing as in claim 31, wherein said backing sheet material is liquid permeable.

33. An external wound dressing as in claim 31, wherein said backing sheet material is liquid impermeable.

* * * * *